(12) United States Patent
Wu

(10) Patent No.: US 11,918,777 B2
(45) Date of Patent: Mar. 5, 2024

(54) SYRINGE PUMP MODULE

(71) Applicant: Chemyx Inc., Stafford, TX (US)

(72) Inventor: Frank Wu, Zhuhai (CN)

(73) Assignee: Chemyx Inc., Stafford, TX (US)

( * ) Notice: Subject to any disclaimer, the term of this patent is extended or adjusted under 35 U.S.C. 154(b) by 185 days.

(21) Appl. No.: 17/590,433

(22) Filed: Feb. 1, 2022

(65) Prior Publication Data

US 2023/0241308 A1 Aug. 3, 2023

(51) Int. Cl.
*A61M 5/142* (2006.01)
*A61M 5/315* (2006.01)

(52) U.S. Cl.
CPC .... *A61M 5/14236* (2013.01); *A61M 5/31585* (2013.01)

(58) Field of Classification Search
CPC .......... A61M 5/14236; A61M 5/14546; A61M 5/31585; A61M 5/1452; A61M 5/1456
See application file for complete search history.

(56) References Cited

U.S. PATENT DOCUMENTS

| | | | |
|---|---|---|---|
| 10,441,713 B1 * | 10/2019 | Feldman | A61M 5/16804 |
| 2004/0195538 A1 * | 10/2004 | Raines | A61M 39/26 251/149.4 |
| 2015/0265764 A1 * | 9/2015 | Weber | A61M 5/16877 604/131 |
| 2017/0095638 A1 * | 4/2017 | Young | A61M 5/20 |
| 2017/0203032 A1 * | 7/2017 | Dowden | A61M 5/168 |
| 2019/0224408 A1 * | 7/2019 | Thomas | A61M 5/1452 |

* cited by examiner

*Primary Examiner* — Dung T Ulsh
(74) *Attorney, Agent, or Firm* — Polsinelli PC

(57) ABSTRACT

Disclosed herein is a syringe pump module with a non-decoupling drive mechanism and motor actuation mechanism to configured to bidirectionally move the non-decoupling drive mechanism.

17 Claims, 3 Drawing Sheets

A-A

SYRINGE PUMP MODULE

FIELD OF TECHNOLOGY

The present disclosure relates generally to high precision pumps designed for dosing highly precise amounts of fluid at low rates for pharmaceutical and chemical applications.

BACKGROUND

Syringe pumps have existed since 1901. In the 1980's digitally controlled syringe pumps were developed in response to the availability of microelectronics that could control the rates of motors which in turned allowed for the development of rate-controlled pumps.

At present, the syringe pumps rely on a screw rod and transmission nut attachment (drive mechanism) to drive a block forward which contacts the plunger to drive the contents out of the syringe. When using the syringe pump, the operator needs to move the push plate to the desired position. The transmission nut is generally divided into two forms of half nut and full nut.

Using a half-nut transmission push plate allows for disengagement, making it is easier to reposition the pusher block plate relative to the position of the screw rod in structure, but compared with the full nut form of the push plate, the following problems will occur: 1) limited pushing force subjected to the force of the spring mechanism, 2) radial friction to increase of the transmission nut leading to fast wear and tear, 3) greater injection flow rate fluctuations due to component variability, 4) reduced accuracy due to limited contact surface between transmission nut and screw rod, and 5) disengagement of the half nut transmission under force, resulting in injection failure.

The use of a full-nut transmission push plate can avoid the above problems, but it is more difficult to realize the permanent engagement of the transmission nut on the screw rod.

SUMMARY

The present disclosure provides syringe pump modules with a non-decoupling drive mechanism and methods for using the syringe pump modules.

In some aspects, the syringe pump module comprises: a housing; a non-decoupling drive mechanism on the outside of the housing; a motor coupled to the non-decoupling drive mechanism; and a motor actuation mechanism connected to the motor and configured to move the non-decoupling drive mechanism bidirectionally.

In some aspects, the non-decoupling drive mechanism comprises a screw rod and a full nut push plate assembly. The full nut push plate assembly comprises: a push plate comprising a first opening and a full nut within the first opening of the push plate. The full nut has a complete thread in the radial direction. The screw rod extends through the full nut and couples to the motor. The full nut is secured within the first opening using at least one screw. The push plate may further comprise a second opening and a third opening, each operable to receive a guide rod. In some aspects, the syringe pump module further comprises one or more guide rods.

In some aspects, the housing comprises a syringe support configured to receive at least one syringe. The at least one syringe is removeable.

In some aspects, the motor actuation mechanism is operable to control the motor to rotate forward and reverse. The motor actuation mechanism is located on an outer surface of the housing. The motor actuation mechanism comprises two buttons, a two-way button, or a two-way knob.

In some aspects, the motor is located in an inner portion located inside the housing. The motor is operable to connect to a controller, wherein the controller is located outside of the housing. The controller may be part of an external system, such as a mass spectrometer, an NMR spectrometer, a liquid chromatography system, an HPLC system, a gas chromatography system, a cytometer, s microscope, ink manufacturing equipment, micro dialysis equipment, a reactor, or a microfluid chip.

In additional aspects, provided herein is a method of preparing an injection from a syringe pump module. The method may comprise: providing a syringe pump module; placing a syringe on the syringe support; and moving the non-decoupling drive mechanism bidirectionally using the motor actuation mechanism. The method may further comprising stopping the non-decoupling drive mechanism when the full nut push plate assembly touches a plunger of the syringe. The method may further comprise connecting the motor to a controller in an external system. The method may further comprise ejecting the contents of the syringe by moving the full nut push plate assembly using the motor connected to the controller.

Other aspects and iterations of the invention are described more thoroughly below.

BRIEF DESCRIPTION OF THE DRAWINGS

In order to describe a manner in which features of the disclosure can be obtained, reference is made to specific embodiments that are illustrated in the appended drawings. Based on an understanding that these drawings depict only example embodiments of the disclosure and are not intended to be limiting of scope, the principles herein are described and explained with additional specificity and detail through the use of the accompanying drawings in which.

DETAILED DESCRIPTION

Figure 1:
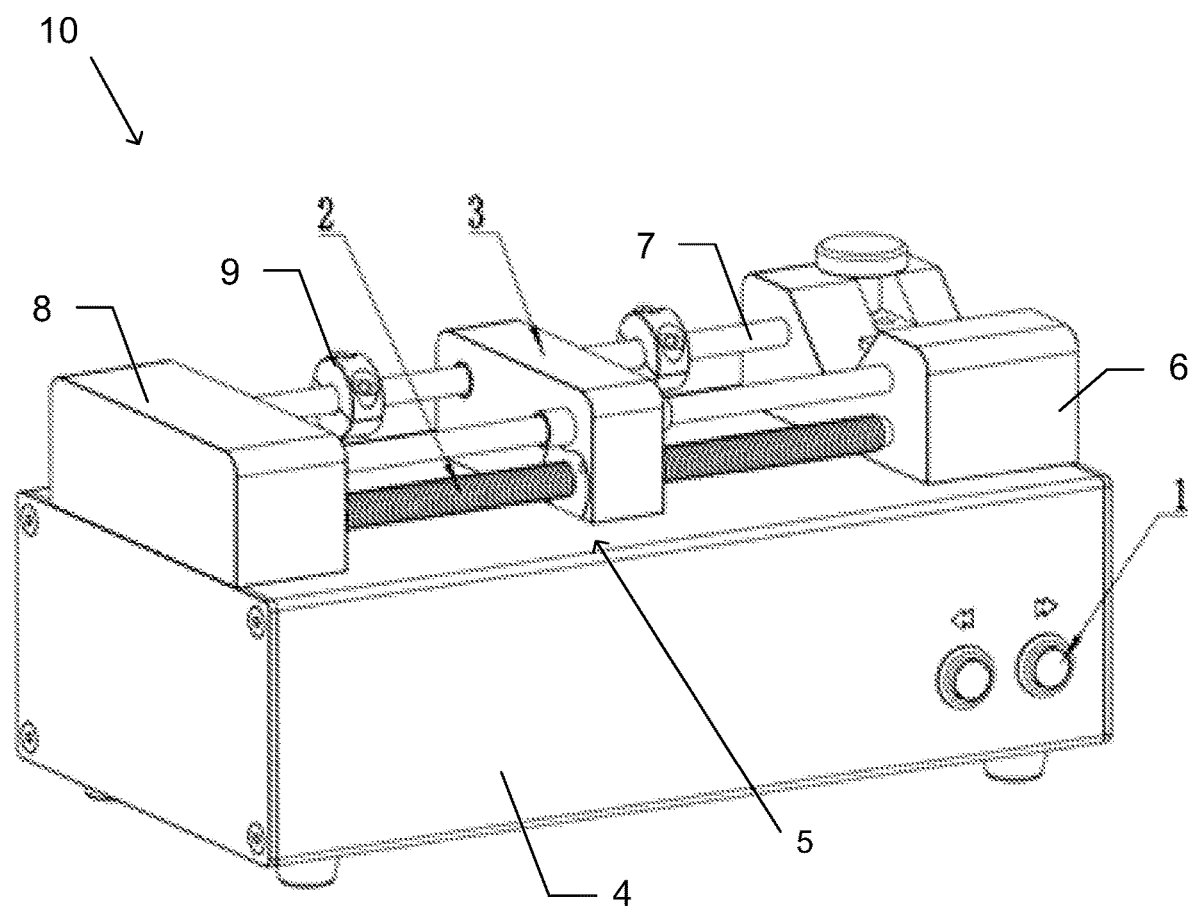
FIG. 1 is a layout diagram of the syringe pump module with a two-way button control mechanism in an embodiment.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described avoid obscuring the description. References to one or an embodiment in the present disclosure can be references to the same embodiment or any embodiment; and, such references mean at least one of the embodiments.

Reference to "one embodiment", "an embodiment", or "an aspect" means that a particular feature, structure, or characteristic described in connection with the embodiment is included in at least one embodiment of the disclosure. The appearances of the phrase "in one embodiment" or "in one aspect" in various places in the specification are not necessarily all referring to the same embodiment, nor are separate or alternative embodiments mutually exclusive of other embodiments. Moreover, various features are described which may be exhibited by some embodiments and not by others.

The use of "adapted to" or "configured to" herein is meant as open and inclusive language that does not foreclose devices adapted to or configured to perform additional tasks or steps.

Moreover, claim language reciting "at least one of" a set indicates that one member of the set or multiple members of the set satisfy the claim. For example, claim language reciting "at least one of A and B" means A, B, or A and B.

Syringe pumps with a half nut mechanism are costly to make and have a short service life due to wear on the half nut. The half nut syringe pumps require manual depression of a button/spring on the push plate to move the pusher plate along the screw rod to the plunger. Currently available syringe pumps with a full nut mechanism require an interface, such as an LCD interface, multiple control buttons, and additional electronics to control movement of the push plate. These additional components significantly add to the cost of full nut syringe pumps.

Provided herein is a syringe pump module with a full nut transmission push plate. The syringe pump module is operable to quickly move the push plate bidirectionally to a desired position using a motor and a motor actuation mechanism. The syringe pump module is an improvement over half nut injection pumps and currently available full nut pumps in that it has wide applicability, convenient operation, and is capable of quick bidirectional movement without decoupling from the screw rod. The syringe pump module described herein is designed to work with other instruments and therefore does not need the additional interfaces and/or electronics required in other full nut syringe pumps. This allows for the syringe pump module to be cheaper, more accurate, have a longer service life, and smoother motion as compared to half nut syringe pumps and more complex full nut syringe pumps. In addition, the ability to independently move the push plate bidirectionally allows for the syringe pump module to be used with any syringe because the syringes can be removeable from the pump. Other full nut syringe pumps require specific, non-removeable syringes to be used with the pump.

The syringe pump module includes a non-decoupling drive mechanism and a motor actuation mechanism to realize the quick bidirectional movement of the push plate using a full nut design. In an embodiment, the syringe pump module includes a housing, a non-decoupling drive mechanism on the outside of the housing, a motor coupled to the non-decoupling drive mechanism, and a motor actuation mechanism connected to the motor and configured to move the non-decoupling drive mechanism bidirectionally (e.g. in a forward and reverse direction). The non-decoupling drive mechanism may include a screw rod and a full nut push plate assembly.

FIG. 1 shows an embodiment of the syringe pump module 10. The syringe pump module 10 includes a housing 4, a non-decoupling drive mechanism 5, and a motor actuation mechanism 1. The non-decoupling drive mechanism 5 includes a screw rod 2 and a push plate assembly 3. The screw rod 2 is connected to the push plate assembly 3 through a full nut in the push plate assembly 3. The non-decoupling drive mechanism 5 is configured such that the screw rod 2 does not decouple from the full nut at any point during operation of the syringe pump module 10 to receive one or more syringes and impart a force on the one or more syringes. The screw rod 2 is connected to a motor located inside the housing 4, and is driven by the motor to rotate axially, so that the push plate assembly 3 is moved forward or backward along the screw rod 2. This provides bidirectional control of the push plate while maintaining engagement of the full nut.

The syringe pump module 10 may further include a syringe support 6 configured to receive at least one syringe. The at least one syringe is removeable from the syringe support 6 and syringe pump module 10. This allows for a variety of syringe sizes and styles to be used with the syringe pump module. The syringe may be secured to the syringe support using a clamp or other mechanism to secure the syringe such that it doesn't move when the push plate presses on the plunger of the syringe.

The syringe support 6 is located on the housing 4. For example, the syringe support 6 may be at one end of the top of the housing 4. The syringe support 6 may also be configured to connect to the screw rod 2 and one or more guide rods 7. The syringe pump module 10 may further include a rod support 8 and one or more guide rods 7. In an example, the rod support 8 may be located on the top of the housing 4 at an end opposite the syringe support 6. The screw rod 2 and one or more guide rods 7 may extend the length of the housing 4 between the syringe support 6 and the end support 8. In an aspect, the screw rod 2 may be connected to the syringe support 6 at a first end and connected to the rod support 8 at a second end. The screw rod 2 may be further connected to the motor at the first end, through the syringe support 6. In another aspect, one or more guide rods 7 may be connected to the syringe support at a first end and connected to the rod support 8 at a second end. The guide rods 7 may include one or more collar clamps 9 that may be placed along the guide rod 7 to limit the full range of movement of the push plate.

Figure 2A:
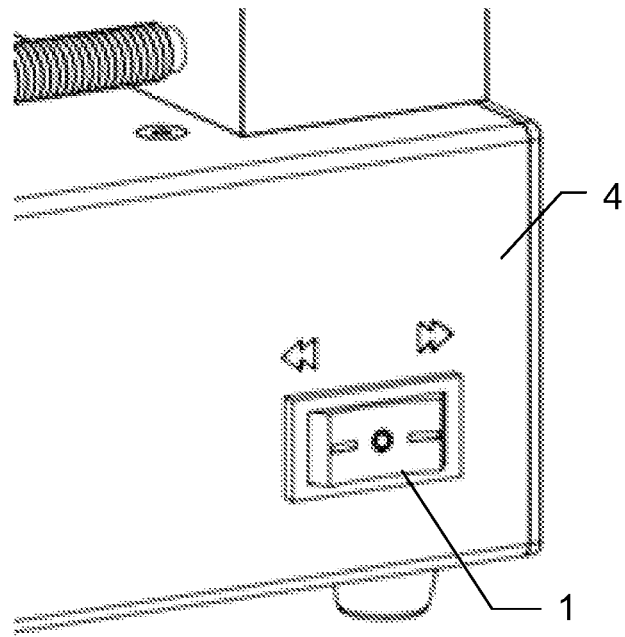
FIG. 2A is a diagrams of a two-way knob control mechanism in an embodiment.
Figure 2B:
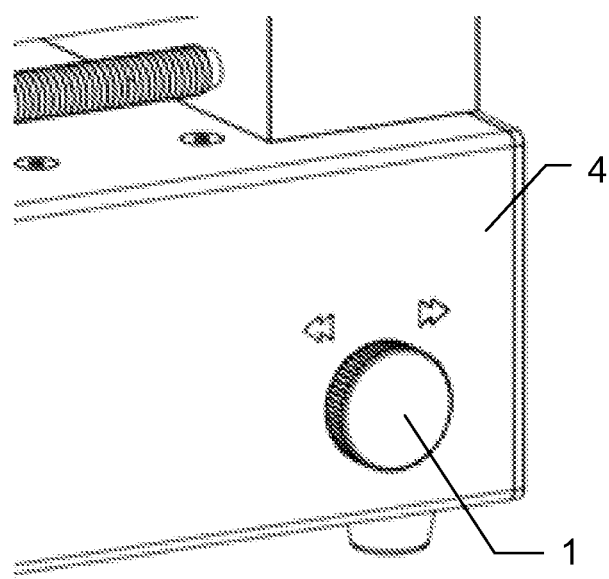
FIG. 2B is a diagram of a button electronic control mechanism in an embodiment.

Referring to FIGS. 1, 2A, and 2B, the motor actuation mechanism 1 is generally located on the outer surface of the housing 4 of the syringe pump module 10. The motor actuation mechanism 1 may include but is not limited to two buttons (FIG. 1), a two-way button (FIG. 2A), a two-way knob (FIG. 2B), a rocker, dial, pulley, knob, torsion switch, rocker switch, shift switch, and any other mechanism actuation mechanism with at least two positions to allow for bidirectional control. In an example, the motor actuation mechanism is two buttons, as seen in FIG. 1, where one button is operable to control the motor to rotate forward, and the other button is operable to control the motor to rotate in reverse. The motor actuation mechanism provides electric control of the push plate assembly 3 to advance or retreat along the screw rod 2 (e.g. bidirectional movement).

Figure 3A:
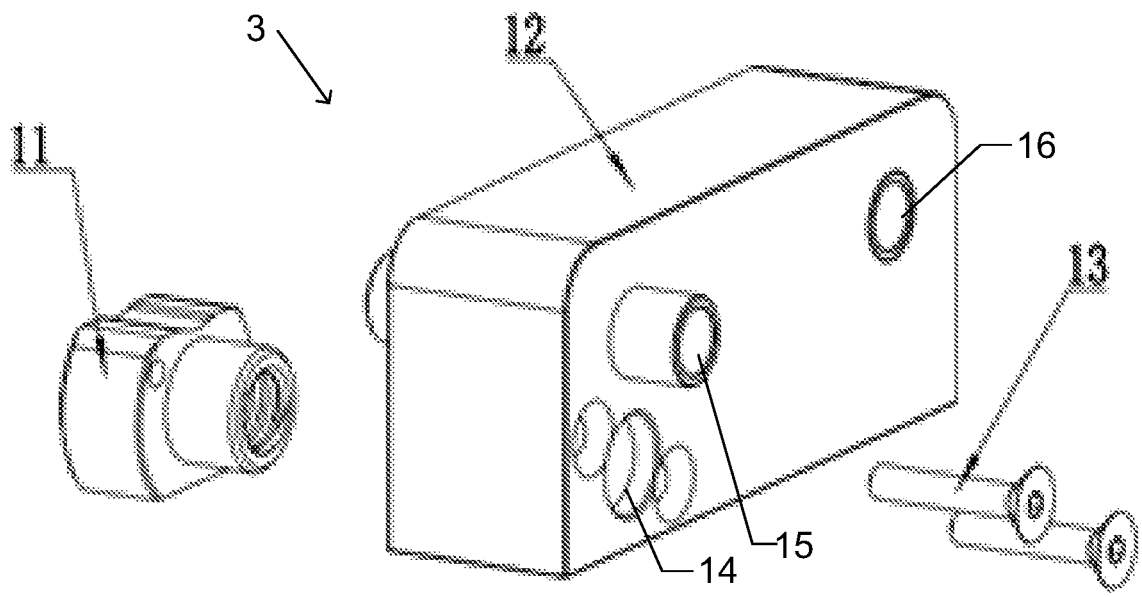
FIG. 3A is an explosion diagram of the full nut push plate in an embodiment.

Referring to FIG. 3A, the push plate assembly 3 includes a full nut 11 and a push plate 12. The push plate 12 includes a first opening 14, a second opening 15, and/or a third opening 16. The full nut 11 is secured within the first opening 14 of the push plate 12 using at least one screw 13. The internal thread of the full nut 11 is a complete thread in the radial direction. The second opening 15 and the third opening 16 are each operable to receive a guide rod (see FIG. 1). The guide rods do not have threading and aid in supporting the push plate 12 along the length of the syringe pump module.

Figure 3B:
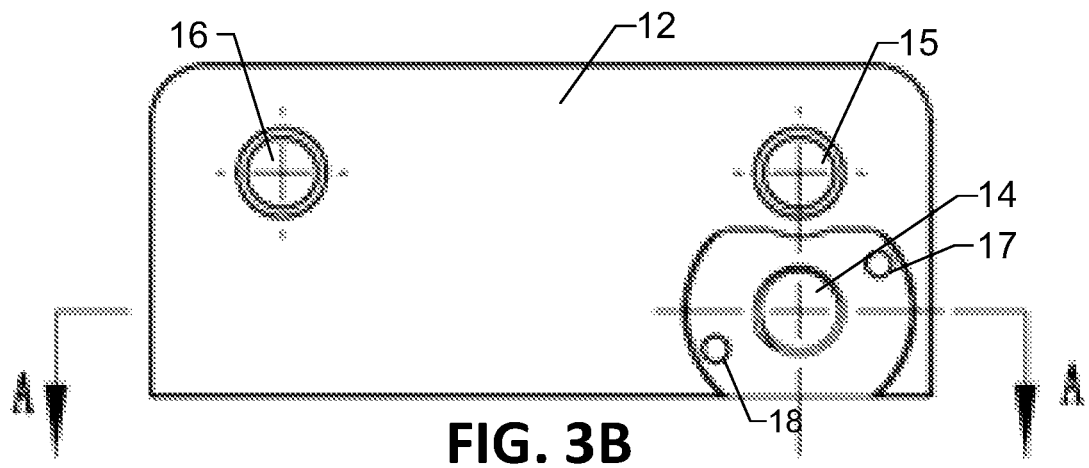
FIG. 3B is a side view of the full nut push plate in an embodiment.

FIG. 3B is a side view of the push plate 12 with the first opening 14, the second opening 15, and the third opening 16. In an example, the first opening 14 may be located in a lower portion of the push plate 12 and the second and third openings 15, 16 may be located in an upper portion of the push plate 12. The second and third openings 15, 16 may be parallel to one another. The first opening 14 may be directly below the second opening 15.

Figure 3C:
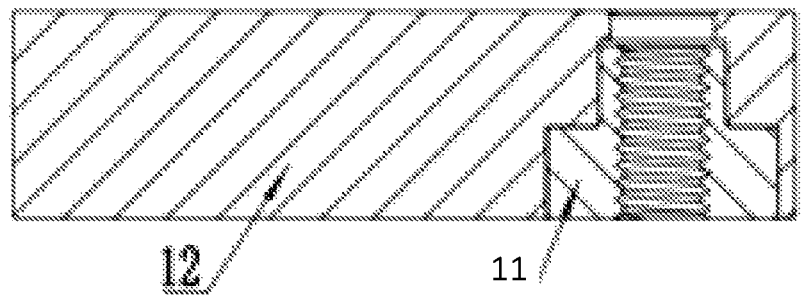
FIG. 3C is a cross-sectional view of the full nut push plate in an embodiment.

FIG. 3C is a cross-sectional view of the push plate 12 that shows the full nut 11 within the first opening such that the full threading of the full nut 11 extends the width of the push plate 12.

In some embodiments, the housing may be an outer enclosure and the motor, electronics, a transmission box, and/or other connector components may be located within an inner portion of the housing. In an embodiment, the housing may be partiality open and therefore the inner portion may not be fully enclosed. In at least one embodiment, the housing may be a plate, allowing the syringe pump module to be attached/embedded in an external system. The push plate assembly may be mounted to the top of the plate, while the motor and other connector components may be mounted below the plate.

The motor is operable to connect to a controller to control delivery of contents of the syringe by controlling the speed of the motor to move the push plate assembly. In various aspects, the controller is located outside of the housing. The syringe pump module may be configured to connect with other external systems and therefore may not need an independent controller in the syringe pump module. Instead, the motor of the syringe pump module may be operable to connect to a controller of the external system for operation. In some embodiments, the controller may be a CPU of an external system. The motor may connect to the controller via wireless, USB, RS232 port to a computer. In some embodiments, the motor actuation mechanism on the external enclosure of the syringe pump module allows the push plate assembly to move without interfacing with a separate controller. The controller in the external system may control delivery from one or more syringes on the syringe pump module. This allows for a simpler, more cost-effective, and longer lasting syringe pump that does not need additional electronics, screens, or controllers. In some examples, the external system may be scientific or manufacturing equipment. Non-limiting examples of external systems include a mass spectrometer, an NMR spectrometer, liquid chromatography systems, HPLC systems, gas chromatography systems, cytometers, microscopes, ink manufacturing equipment, micro dialysis equipment, reactors, microfluid chips, or any other laboratory equipment operable to integrate with a syringe pump module.

Further provided herein is a method of preparing an injection from a syringe pump module. The method may include providing a syringe pump module, placing a syringe on the syringe support, and moving the non-decoupling drive mechanism bidirectionally using the motor actuation mechanism. In some aspects, the method may further include stopping the non-decoupling drive mechanism when the full nut push plate assembly touches a plunger of the syringe, connecting the motor to a controller in an external system, and/or ejecting the contents of the syringe by moving the full nut push plate assembly using the motor connected to the controller.

The above is only a preferred embodiment of the present invention, and does not limit the technical scope of the present invention. Therefore, any minor modifications, equivalent changes and modifications made to the above examples based on the technical essence of the present invention all fall within the scope of the technical solution of the present invention. Additionally, a number of well-known processes and elements have not been described in order to avoid unnecessarily obscuring the present disclosure. Accordingly, the above description should not be taken as limiting the scope of the disclosure.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A syringe pump module comprising:
   a housing;
   a non-decoupling drive mechanism on an outside of the housing, the non-decoupling drive mechanism comprising:
     a screw rod; and
     a full nut push plate assembly, the full nut push plate assembly comprising:
       a push plate comprising:
         a first opening;
         a second opening operable to receive a first guide rod; and
         a third opening operable to receive a second guide rod; and
       a full nut within the first opening of the push plate;
   a motor coupled to the non-decoupling drive mechanism; and
   a motor actuation mechanism connected to the motor and configured to move the non-decoupling drive mechanism bidirectionally.

2. The syringe pump module of claim 1, wherein the motor is located in an inner portion located inside the housing.

3. The syringe pump module of claim 1, wherein the full nut has a complete thread in a radial direction.

4. The syringe pump module of claim 1, wherein the screw rod extends through the full nut and couples to the motor.

5. The syringe pump module of claim 1, wherein the full nut is secured within the first opening using at least one screw.

6. The syringe pump module of claim 1, wherein the housing comprises a syringe support configured to receive at least one syringe.

7. The syringe pump module of claim 6, wherein the at least one syringe is removeable.

8. The syringe pump module of claim 1, wherein the motor actuation mechanism is operable to control the motor to rotate forward and reverse.

9. The syringe pump module of claim 1, wherein the motor actuation mechanism is located on an outer surface of the housing.

10. The syringe pump module of claim 1, wherein the motor actuation mechanism comprises two buttons, a two-way button, or a two-way knob.

11. The syringe pump module of claim 1, wherein the motor is operable to connect to a controller, wherein the controller is located outside of the housing.

12. The syringe pump module of claim 11, wherein the controller is part of an external system.

13. The syringe pump module of claim 12, wherein the external system is a mass spectrometer, an NMR spectrometer, a liquid chromatography system, an HPLC system, a gas chromatography system, a cytometer, a microscope, ink manufacturing equipment, micro dialysis equipment, a reactor, or a microfluid chip.

14. A method of preparing an injection from a syringe pump module, the method comprising:
  providing a syringe pump module comprising:
    a syringe support on a housing;
    a non-decoupling drive mechanism on the housing, the non-decoupling drive mechanism comprising:
      a screw rod; and
      a full nut push plate assembly, the full nut push plate assembly comprising:
        a push plate comprising:
          a first opening;
          a second opening operable to receive a first guide rod; and
          a third opening operable to receive a second guide rod; and
        a full nut within the first opening of the push plate;
      a motor inside the housing and coupled to the non-decoupling drive mechanism; and
      a motor actuation mechanism connected to the motor;
  placing the syringe on the syringe support; and
  moving the non-decoupling drive mechanism bidirectionally using the motor actuation mechanism.

15. The method of claim 14, further comprising stopping the non-decoupling drive mechanism when the full nut push plate assembly touches a plunger of the syringe.

16. The method of claim 15, further comprising connecting the motor to a controller in an external system.

17. The method of claim 16, further comprising ejecting the contents of the syringe by moving the full nut push plate assembly using the motor connected to the controller.

* * * * *